United States Patent
Suzuki et al.

(10) Patent No.: US 8,283,338 B2
(45) Date of Patent: Oct. 9, 2012

(54) GIP SECRETION INHIBITOR

(75) Inventors: Junko Suzuki, Haga-gun (JP); Akira Shimotoyodome, Haga-gun (JP); Tomohisa Ichiba, Sumida-ku (JP)

(73) Assignee: Kao Corporation, Tokyo (JP)

( * ) Notice: Subject to any disclaimer, the term of this patent is extended or adjusted under 35 U.S.C. 154(b) by 752 days.

(21) Appl. No.: 12/325,039

(22) Filed: Nov. 28, 2008

(65) Prior Publication Data

US 2009/0143329 A1   Jun. 4, 2009

(30) Foreign Application Priority Data

Nov. 30, 2007 (JP) .................................. 2007-310998
Nov. 26, 2008 (JP) .................................. 2008-301016

(51) Int. Cl.
*A01N 43/04* (2006.01)
*A61K 31/715* (2006.01)

(52) U.S. Cl. ......................................................... 514/54

(58) Field of Classification Search ........................ None
See application file for complete search history.

(56) References Cited

U.S. PATENT DOCUMENTS

| | | | |
|---|---|---|---|
| 4,348,420 A | 9/1982 | Lynch et al. | |
| 4,673,582 A | 6/1987 | Nofre et al. | |
| 4,877,895 A | 10/1989 | Nofre et al. | |
| 5,034,378 A | 7/1991 | Cox | |
| 5,082,684 A | 1/1992 | Fung | |
| 5,158,798 A | 10/1992 | Fung et al. | |
| 5,273,753 A | 12/1993 | Ishihara et al. | |
| 5,308,639 A | 5/1994 | Fung | |
| 5,460,957 A | 10/1995 | Hiura et al. | |
| 5,516,666 A | 5/1996 | Nozomi et al. | |
| 5,609,896 A | 3/1997 | Cox et al. | |
| 5,626,901 A | 5/1997 | Ambjerg Pedersen | |
| 5,641,533 A | 6/1997 | Ambjerg Pedersen | |
| 5,693,624 A * | 12/1997 | Hardy et al. ................... | 514/54 |
| 5,718,920 A | 2/1998 | Notenbomer | |
| 5,770,217 A | 6/1998 | Kutilek, III et al. | |
| 5,776,929 A * | 7/1998 | Hagishita et al. ............ | 514/221 |
| 5,922,379 A | 7/1999 | Wang | |
| 6,136,349 A | 10/2000 | Karppanen et al. | |
| 6,171,624 B1 | 1/2001 | Reddy et al. | |
| 6,248,390 B1 | 6/2001 | Stillman | |
| 6,306,449 B1 | 10/2001 | Reddy et al. | |
| 6,379,725 B1 | 4/2002 | Wang et al. | |
| 6,455,083 B1 | 9/2002 | Wang | |
| 6,572,898 B2 | 6/2003 | Nelson et al. | |
| 6,645,536 B2 | 11/2003 | D'Abramo | |
| 6,770,305 B2 | 8/2004 | Nelson et al. | |
| 6,815,433 B2 | 11/2004 | Hansson et al. | |
| 6,815,436 B2 | 11/2004 | Hansson et al. | |
| 6,835,015 B2 | 12/2004 | Pearce | |
| 6,884,445 B2 | 4/2005 | Navarro Y Koren et al. | |
| 6,905,431 B2 | 6/2005 | Pearce et al. | |
| 6,929,807 B1 | 8/2005 | McAnalley et al. | |
| 7,115,297 B2 | 10/2006 | Stillman | |
| 7,157,431 B2 | 1/2007 | McAnalley et al. | |
| 7,196,064 B2 | 3/2007 | McAnalley et al. | |
| 7,199,104 B2 | 4/2007 | McAnalley et al. | |
| 7,202,220 B2 | 4/2007 | McAnalley et al. | |
| 7,238,380 B2 | 7/2007 | Stillman | |
| 7,550,436 B2 | 6/2009 | Takahashi et al. | |
| 7,666,448 B2 | 2/2010 | Mower | |
| 7,700,144 B2 | 4/2010 | Pandey et al. | |
| 7,722,902 B2 | 5/2010 | Mower | |
| 7,749,545 B2 | 7/2010 | Mower | |
| 7,776,365 B2 | 8/2010 | Mower | |
| 7,838,004 B2 | 11/2010 | Mower | |
| 7,892,586 B2 | 2/2011 | Stillman | |
| 7,972,620 B2 | 7/2011 | Andersen et al. | |
| 8,097,271 B2 | 1/2012 | Lakkis et al. | |
| 8,101,208 B2 | 1/2012 | Lakkis et al. | |
| 2002/0009502 A1 | 1/2002 | Nelson et al. | |
| 2002/0094971 A1 | 7/2002 | Hansson et al. | |
| 2002/0192335 A1 | 12/2002 | D'Abramo | |
| 2003/0004135 A1 | 1/2003 | Hansson et al. | |
| 2003/0062315 A1 * | 4/2003 | Cornelius et al. ............ | 210/698 |
| 2003/0064104 A1 | 4/2003 | Stillman | |
| 2003/0072770 A1 | 4/2003 | McAnalley et al. | |
| 2003/0118712 A1 | 6/2003 | Navarro Y Koren et al. | |
| 2003/0144179 A1 | 7/2003 | Takahashi et al. | |
| 2003/0157107 A1 | 8/2003 | Miyawaki et al. | |

(Continued)

FOREIGN PATENT DOCUMENTS

AT            197375 A        4/1978

(Continued)

OTHER PUBLICATIONS

Raghavendran et al., "Efficacy of Brown Seaweed Hot Water Extract Against HCl-ethanol Induced Gastric Mucosal Injury in Rats", Arch Pharm Res., vol. 27, No. 4, 44-453, 2004.*
Database WPI Week 200709, Thomson Scientific, AN 2007-086835, / JP 2006-342085, XP002513039, Dec. 21, 2006, 2 Pages.
Database WPI Week 200781, Thomson Scientific, AN 2007-882743, / JP 2007-122801, XP002513040, Nov. 1, 2007, 2 Pages.
Database WPI Week 200657, Thomson Scientific, AN 2006-554163, / JP 2006-206474, XP002513041, Aug. 10, 2006, 2 Pages.
Database WPI Week 200660, Thomson Scientific, AN 2006-582693, / JP 2006-219492, XP002513042, Aug. 24, 2006, 2 Pages.
J. C. Brown, et al., "Preparation of highly active enterogastrone[1]", Canadian Journal of Physiology and Pharmacology, vol. 47, 1969, pp. 113-114.

(Continued)

*Primary Examiner* — Traviss C McIntosh, III
(74) *Attorney, Agent, or Firm* — Oblon, Spivak, McClelland, Maier & Neustadt, L.L.P.

(57) ABSTRACT

The present invention provides a postprandial GIP secretion inhibitor comprising potassium alginate as an active ingredient. The postprandial GIP secretion inhibitor of the present invention is useful as a medicine or a food product. The present invention also provides use of potassium alginate for the manufacture of a postprandial GIP secretion inhibitor. The present invention also provides a method for inhibiting postprandial GIP secretion, which comprises administering potassium alginate to a subject in need thereof or causing a subject in need thereof to consume potassium alginate.

17 Claims, No Drawings

U.S. PATENT DOCUMENTS

| | | |
|---|---|---|
| 2003/0175345 A1 | 9/2003 | Hite et al. |
| 2003/0198726 A1 | 10/2003 | Navarro Y Koren et al. |
| 2003/0203048 A1 | 10/2003 | Nelson et al. |
| 2003/0211201 A1 | 11/2003 | Stillman |
| 2003/0224090 A1 | 12/2003 | Pearce et al. |
| 2003/0235453 A1 | 12/2003 | Pearce |
| 2003/0235662 A1 | 12/2003 | Pearce et al. |
| 2004/0076614 A1 | 4/2004 | Schur |
| 2004/0170706 A1 | 9/2004 | McAnalley et al. |
| 2004/0171583 A1 | 9/2004 | McAnalley et al. |
| 2004/0198699 A1 | 10/2004 | Hansson et al. |
| 2004/0224068 A1 | 11/2004 | Lee |
| 2004/0247746 A1 | 12/2004 | Pearce et al. |
| 2005/0008713 A1 | 1/2005 | McAnalley et al. |
| 2005/0008735 A1 | 1/2005 | Pearce |
| 2005/0013902 A1 | 1/2005 | Pearce |
| 2005/0070502 A1 | 3/2005 | Hansson et al. |
| 2005/0074525 A1 | 4/2005 | Pearce |
| 2005/0074526 A1 | 4/2005 | Pearce |
| 2005/0100639 A1 | 5/2005 | Pearce |
| 2005/0100647 A1 | 5/2005 | Pearce |
| 2005/0100648 A1 | 5/2005 | Pearce |
| 2005/0100651 A1 | 5/2005 | Pearce |
| 2005/0106233 A1 | 5/2005 | Andersen et al. |
| 2005/0118326 A1 | 6/2005 | Anfinsen et al. |
| 2005/0175735 A1 | 8/2005 | Gandhi et al. |
| 2006/0034894 A1 | 2/2006 | Lakkis et al. |
| 2006/0034936 A1 | 2/2006 | Lakkis et al. |
| 2006/0051296 A1 | 3/2006 | Holahan |
| 2006/0193956 A1 | 8/2006 | Leshik et al. |
| 2006/0210496 A1 | 9/2006 | Mower |
| 2006/0210514 A1 | 9/2006 | Mower |
| 2006/0210515 A1 | 9/2006 | Mower |
| 2006/0210516 A1 | 9/2006 | Mower |
| 2006/0210517 A1 | 9/2006 | Mower |
| 2006/0210524 A1 | 9/2006 | Mower |
| 2006/0210609 A1 | 9/2006 | Mower |
| 2006/0210621 A1 | 9/2006 | Mower |
| 2006/0210688 A1 | 9/2006 | Mower |
| 2006/0210692 A1 | 9/2006 | Mower |
| 2006/0210697 A1 | 9/2006 | Mower |
| 2006/0211652 A1 | 9/2006 | Mower |
| 2006/0234948 A1 | 10/2006 | Empie et al. |
| 2007/0009576 A1 | 1/2007 | Stillman |
| 2007/0020358 A1 | 1/2007 | Mower |
| 2007/0026129 A1 | 2/2007 | Pandey et al. |
| 2007/0042103 A1 | 2/2007 | Cho et al. |
| 2007/0042104 A1 | 2/2007 | Cho et al. |
| 2007/0042106 A1 | 2/2007 | Wagner et al. |
| 2007/0042107 A1 | 2/2007 | Kenneth et al. |
| 2007/0082025 A1 | 4/2007 | Catani et al. |
| 2007/0082026 A1 | 4/2007 | Aimutis, Jr. et al. |
| 2007/0082028 A1 | 4/2007 | Aimutis, Jr. et al. |
| 2007/0082029 A1 | 4/2007 | Aimutis et al. |
| 2007/0082084 A1 | 4/2007 | Catani et al. |
| 2007/0082107 A1 | 4/2007 | Aimutis, Jr. et al. |
| 2007/0082108 A1 | 4/2007 | Aimutis, Jr. et al. |
| 2007/0082114 A1 | 4/2007 | Catani |
| 2007/0087036 A1 | 4/2007 | Durschlag et al. |
| 2007/0087038 A1 | 4/2007 | Richardson et al. |
| 2007/0116800 A1 | 5/2007 | Prakash et al. |
| 2007/0116819 A1 | 5/2007 | Prakash et al. |
| 2007/0116820 A1 | 5/2007 | Prakash et al. |
| 2007/0116821 A1 | 5/2007 | Prakash et al. |
| 2007/0116822 A1 | 5/2007 | Prakash et al. |
| 2007/0116823 A1 | 5/2007 | Prakash et al. |
| 2007/0116824 A1 | 5/2007 | Prakash et al. |
| 2007/0116825 A1 | 5/2007 | Prakash et al. |
| 2007/0116826 A1 | 5/2007 | Prakash et al. |
| 2007/0116827 A1 | 5/2007 | Prakash et al. |
| 2007/0116828 A1 | 5/2007 | Prakash et al. |
| 2007/0116829 A1 | 5/2007 | Prakash et al. |
| 2007/0116830 A1 | 5/2007 | Prakash et al. |
| 2007/0116831 A1 | 5/2007 | Prakash et al. |
| 2007/0116832 A1 | 5/2007 | Prakash et al. |
| 2007/0116833 A1 | 5/2007 | Prakash et al. |
| 2007/0116834 A1 | 5/2007 | Prakash et al. |
| 2007/0116835 A1 | 5/2007 | Prakash et al. |
| 2007/0116836 A1 | 5/2007 | Prakash et al. |
| 2007/0116837 A1 | 5/2007 | Prakash et al. |
| 2007/0116838 A1 | 5/2007 | Prakash et al. |
| 2007/0116839 A1 | 5/2007 | Prakash et al. |
| 2007/0116840 A1 | 5/2007 | Prakash et al. |
| 2007/0116841 A1 | 5/2007 | Prakash et al. |
| 2007/0134390 A1 | 6/2007 | Prakash et al. |
| 2007/0134391 A1 | 6/2007 | Prakash et al. |
| 2007/0148324 A1 | 6/2007 | Lin et al. |
| 2007/0149478 A1 | 6/2007 | McAnalley et al. |
| 2007/0151569 A1 | 7/2007 | Catani et al. |
| 2007/0160735 A1 | 7/2007 | Stillman |
| 2007/0178140 A1 | 8/2007 | Aimutis, Jr. et al. |
| 2007/0196539 A1 | 8/2007 | Yang et al. |
| 2007/0224321 A1 | 9/2007 | Prakash et al. |
| 2007/0275118 A1 | 11/2007 | Van Laere et al. |
| 2007/0281056 A1 | 12/2007 | Whittle et al. |
| 2008/0014327 A1 | 1/2008 | Stillman |
| 2008/0026038 A1 | 1/2008 | Steele et al. |
| 2008/0031928 A1 | 2/2008 | Steele et al. |
| 2008/0089978 A1 | 4/2008 | Grigg et al. |
| 2008/0166453 A1 | 7/2008 | Steele et al. |
| 2008/0175957 A1 | 7/2008 | Horgan et al. |
| 2009/0004220 A1 | 1/2009 | McAnalley et al. |
| 2009/0035436 A1 | 2/2009 | Leshik et al. |
| 2009/0074917 A2 | 3/2009 | Steele et al. |
| 2009/0143329 A1 | 6/2009 | Suzuki et al. |
| 2009/0155409 A1 | 6/2009 | Sexton et al. |
| 2009/0169682 A1 | 7/2009 | Okumura et al. |
| 2009/0181145 A1 | 7/2009 | Pandev et al. |
| 2009/0274791 A1 | 11/2009 | Mattson et al. |
| 2010/0055281 A1 | 3/2010 | Barrow et al. |
| 2010/0256090 A1 | 10/2010 | Yu et al. |
| 2010/0260904 A1 | 10/2010 | Aimutis et al. |
| 2010/0330211 A1 | 12/2010 | Mower |
| 2011/0008485 A1 | 1/2011 | Minor et al. |
| 2011/0021421 A1 | 1/2011 | Kiers et al. |
| 2011/0038982 A1 | 2/2011 | Sliwinski et al. |
| 2011/0038984 A1 | 2/2011 | Anfinsen et al. |
| 2011/0059165 A1 | 3/2011 | Gaserod et al. |
| 2011/0059166 A1 | 3/2011 | Gaserod et al. |
| 2011/0104336 A1 | 5/2011 | Stillman |
| 2011/0135568 A1 | 6/2011 | Holahan |
| 2011/0135799 A1 | 6/2011 | Holahan |
| 2011/0151094 A1 | 6/2011 | Foo et al. |
| 2011/0195101 A1 | 8/2011 | Andersen et al. |
| 2011/0200732 A1 | 8/2011 | Kielmeyer et al. |
| 2011/0257089 A1 | 10/2011 | Huisman et al. |
| 2012/0015039 A1 | 1/2012 | Sexton et al. |

FOREIGN PATENT DOCUMENTS

| | | |
|---|---|---|
| AT | 347037 B | 12/1978 |
| AT | 41288 T | 4/1989 |
| AT | 49700 T | 2/1990 |
| AT | 162958 T | 2/1998 |
| AT | 188380 T | 1/2000 |
| AT | 218065 T | 6/2002 |
| AT | 237956 T | 5/2003 |
| AT | 311763 T | 12/2005 |
| AT | 355068 T | 3/2006 |
| AT | 334688 T | 8/2006 |
| AT | 394096 T | 5/2008 |
| AT | 406875 T | 9/2008 |
| AT | 421338 T | 2/2009 |
| AT | 471084 T | 7/2010 |
| AT | 515951 T | 7/2011 |
| AU | 7381981 A | 3/1982 |
| AU | 5440786 A | 9/1987 |
| AU | 6025986 A | 1/1988 |
| AU | 571773 B2 | 4/1988 |
| AU | 591148 B2 | 11/1989 |
| AU | 703527 B2 | 3/1990 |
| AU | 7023899 | 8/1991 |
| AU | 7415891 A | 10/1991 |
| AU | 6750294 A | 1/1995 |
| AU | 5719394 A | 6/1995 |
| AU | 660812 B2 | 7/1995 |
| AU | 1467695 A | 8/1995 |
| AU | 5176796 | 10/1996 |

| AU | 675542 B2 | 2/1997 | CA | 2046345 C | 8/1996 |
| --- | --- | --- | --- | --- | --- |
| AU | 679708 | 7/1997 | CA | 2182061 A1 | 2/1997 |
| AU | 2355297 | 11/1997 | CA | 2182249 | 2/1997 |
| AU | 3819997 | 3/1998 | CA | 2205517 A1 | 11/1997 |
| AU | 5399798 A | 7/1998 | CA | 2 262 972 A1 | 2/1998 |
| AU | 5399898 A | 7/1998 | CA | 2276011 A1 | 7/1998 |
| AU | 3642699 A | 11/1999 | CA | 2369946 A1 | 11/2000 |
| AU | 4543700 | 11/2000 | CA | 2373473 A1 | 11/2000 |
| AU | 4992399 A | 12/2000 | CA | 2399918 A1 | 8/2001 |
| AU | 734183 B2 | 6/2001 | CA | 2422900 A1 | 5/2002 |
| AU | 735035 B2 | 6/2001 | CA | 2437530 A1 | 9/2002 |
| AU | 3982101 A | 9/2001 | CA | 2484528 A1 | 6/2003 |
| AU | 734183 C | 11/2001 | CA | 2509715 A1 | 8/2004 |
| AU | 5268901 A | 11/2001 | CA | 2509715 C | 8/2004 |
| AU | 9619601 A | 5/2002 | CA | 2694872 A1 | 8/2004 |
| AU | 2002366638 A1 | 6/2003 | CA | 2521531 A1 | 11/2004 |
| AU | 2003219623 A1 | 10/2003 | CA | 2530216 A1 | 11/2004 |
| AU | 2003297428 A1 | 7/2004 | CA | 2708045 A1 | 11/2004 |
| AU | 2003297428 A8 | 7/2004 | CA | 2714572 A1 | 11/2004 |
| AU | 2004209974 A1 | 8/2004 | CA | 2529491 A1 | 12/2004 |
| AU | 2003236156 A1 | 1/2005 | CA | 2 584 188 A1 | 4/2005 |
| AU | 2003304197 A1 | 1/2005 | CA | 2 576 344 A1 | 2/2006 |
| AU | 2004281184 C1 | 4/2005 | CA | 2 576 344 C | 2/2006 |
| AU | 782727 B2 | 8/2005 | CA | 2 576 375 A1 | 2/2006 |
| AU | 2005213302 A1 | 8/2005 | CA | 2 576 375 C | 2/2006 |
| AU | 2005272802 A1 | 2/2006 | CA | 2276011 C | 3/2006 |
| AU | 2005272802 B2 | 2/2006 | CA | 2 499 442 A1 | 8/2006 |
| AU | 2005272922 B2 | 2/2006 | CA | 2 601 315 A1 | 9/2006 |
| AU | 2001296196 B2 | 7/2006 | CA | 2 604 595 A1 | 10/2006 |
| AU | 782727 C | 9/2006 | CA | 2 606 724 A1 | 11/2006 |
| AU | 2006227390 A1 | 9/2006 | CA | 2 552 313 A1 | 1/2007 |
| AU | 2002244694 B2 | 10/2006 | CA | 2 552 313 C | 1/2007 |
| AU | 2006232344 A1 | 10/2006 | CA | 2 614 348 A1 | 1/2007 |
| AU | 2006242246 A1 | 11/2006 | CA | 2 615 646 A1 | 2/2007 |
| AU | 2006269568 A1 | 1/2007 | CA | 2 629 983 A1 | 5/2007 |
| AU | 2006279487 A1 | 2/2007 | CA | 2 630 042 A1 | 5/2007 |
| AU | 2006316309 A1 | 5/2007 | CA | 2 630 043 A1 | 5/2007 |
| AU | 2006316313 A1 | 5/2007 | CA | 2 630 048 A1 | 5/2007 |
| AU | 2006318698 A1 | 5/2007 | CA | 2 630 051 A1 | 5/2007 |
| AU | 2006318700 A1 | 5/2007 | CA | 2 630 052 A1 | 5/2007 |
| AU | 2006318708 A1 | 5/2007 | CA | 2 630 054 A1 | 5/2007 |
| AU | 2006318711 A1 | 5/2007 | CA | 2 630 055 A1 | 5/2007 |
| AU | 2006318712 A1 | 5/2007 | CA | 2 630 056 A1 | 5/2007 |
| AU | 2006318751 A1 | 5/2007 | CA | 2 630 059 A1 | 5/2007 |
| AU | 2006318752 A1 | 5/2007 | CA | 2 630 060 A1 | 5/2007 |
| AU | 2006318753 A1 | 5/2007 | CA | 2 630 080 A1 | 5/2007 |
| AU | 2006318764 A1 | 5/2007 | CA | 2 630 131 A1 | 5/2007 |
| AU | 2006318765 A1 | 5/2007 | CA | 2 630 141 A1 | 5/2007 |
| AU | 2006318766 A1 | 5/2007 | CA | 2 630 142 A1 | 5/2007 |
| AU | 2006318783 A1 | 5/2007 | CA | 2 630 143 A1 | 5/2007 |
| AU | 2006318788 A1 | 5/2007 | CA | 2 630 144 A1 | 5/2007 |
| AU | 2006318790 A1 | 5/2007 | CA | 2 630 145 A1 | 5/2007 |
| AU | 2006318795 A1 | 5/2007 | CA | 2 629 974 A1 | 6/2007 |
| AU | 2006318796 A1 | 5/2007 | CA | 2 630 208 A1 | 10/2007 |
| AU | 2006325130 A1 | 6/2007 | CA | 2 643 662 A1 | 10/2007 |
| AU | 2004209974 B2 | 7/2007 | CA | 2 630 031 A1 | 12/2007 |
| AU | 2007217851 A1 | 8/2007 | CA | 2373473 C | 2/2008 |
| AU | 2006341542 A1 | 10/2007 | CA | 2 262 972 C | 7/2008 |
| AU | 2007238985 A1 | 10/2007 | CA | 2 674 422 A1 | 7/2008 |
| AU | 2006344337 A1 | 12/2007 | CA | 2733901 | 3/2010 |
| AU | 2001239821 C1 | 3/2008 | CA | 2 740 910 A1 | 4/2010 |
| AU | 2007317460 A1 | 5/2008 | CA | 2509715 C | 5/2010 |
| AU | 2008206670 A1 | 7/2008 | CA | 2 747 659 A1 | 7/2010 |
| AU | 2008361201 A1 | 3/2010 | CA | 2530216 C | 8/2010 |
| AU | 2009304323 A1 | 4/2010 | CA | 2 756 765 | 10/2010 |
| AU | 2004281184 B2 | 6/2011 | CA | 2529491 C | 10/2011 |
| AU | 2009335743 A1 | 8/2011 | CH | 610731 A5 | 5/1979 |
| AU | 2010233000 A1 | 10/2011 | CN | 86101752 A | 10/1986 |
| BE | 826675 A1 | 9/1975 | CN | 1010584 B | 11/1990 |
| CA | 1041013 A1 | 10/1978 | CN | 1104890 A | 7/1995 |
| CA | 1263404 A1 | 11/1989 | CN | 1122101 | 6/1996 |
| CA | 2166735 C | 7/1990 | CN | 1179705 | 4/1998 |
| CA | 2035529 A1 | 10/1991 | CN | 1227495 A | 9/1999 |
| CA | 2035529 C | 10/1991 | CN | 1241912 A | 1/2000 |
| CA | 2039947 | 10/1991 | CN | 1061514 C | 2/2001 |
| CA | 2128160 A1 | 1/1995 | CN | 1284297 A | 2/2001 |
| CA | 2177466 A1 | 6/1995 | CN | 1299238 A | 6/2001 |
| CA | 2166735 | 7/1996 | CN | 1086277 C | 6/2002 |
| CA | 2046345 A1 | 8/1996 | CN | 1404364 A | 3/2003 |

| | | | | | | |
|---|---|---|---|---|---|---|
| CN | 1115966 | C | 7/2003 | EP | 0 195 731 A2 | 9/1986 |
| CN | 1431870 | A | 7/2003 | EP | 0 195 731 A3 | 9/1986 |
| CN | 1457704 | A | 11/2003 | EP | 0 195 731 B1 | 9/1986 |
| CN | 1211019 | C | 7/2005 | EP | 0 195 730 A3 | 7/1987 |
| CN | 1655769 | A | 8/2005 | EP | 0441495 A2 | 8/1991 |
| CN | 1221188 | C | 10/2005 | EP | 0 452 262 A2 | 10/1991 |
| CN | 1695488 | A | 11/2005 | EP | 0 457 919 A1 | 11/1991 |
| CN | 1777415 | A | 5/2006 | EP | 0 457 919 A4 | 11/1991 |
| CN | 1787750 | A | 6/2006 | EP | 0 452 262 A3 | 4/1992 |
| CN | 1262213 | C | 7/2006 | EP | 0441495 A3 | 9/1992 |
| CN | 1819815 | A | 8/2006 | EP | 0 648 495 A2 | 4/1995 |
| CN | 1852659 | A | 10/2006 | EP | 0 648 495 A3 | 8/1995 |
| CN | 1879507 | A | 12/2006 | EP | 0 452 262 B1 | 1/1996 |
| CN | 101001536 | A | 7/2007 | EP | 0 730 494 A1 | 9/1996 |
| CN | 101001537 | A | 7/2007 | EP | 0 743 011 A1 | 11/1996 |
| CN | 101011082 | A | 8/2007 | EP | 0 757 895 A2 | 2/1997 |
| CN | 101166544 | A | 4/2008 | EP | 0 758 831 A2 | 2/1997 |
| CN | 101171037 | A | 4/2008 | EP | 0 757 895 A3 | 7/1997 |
| CN | 101188948 | A | 5/2008 | EP | 0 758 531 A3 | 7/1997 |
| CN | 101242744 | A | 8/2008 | EP | 0 808 580 A2 | 11/1997 |
| CN | 101287382 | A | 10/2008 | EP | 0 808 580 A3 | 11/1997 |
| CN | 101291589 | A | 10/2008 | EP | 0 730 494 B1 | 2/1998 |
| CN | 101306011 | A | 11/2008 | EP | 0743011 A4 | 10/1998 |
| CN | 101309598 | A | 11/2008 | EP | 0 923 382 A1 | 6/1999 |
| CN | 101309599 | A | 11/2008 | EP | 0 923 382 A4 | 6/1999 |
| CN | 101309600 | A | 11/2008 | EP | 0 948 265 A1 | 10/1999 |
| CN | 101309601 | A | 11/2008 | EP | 0 648 495 B1 | 1/2000 |
| CN | 101309602 | A | 11/2008 | EP | 1 075 188 A1 | 2/2001 |
| CN | 101312653 | A | 11/2008 | EP | 1 075 188 A4 | 2/2001 |
| CN | 101312658 | A | 11/2008 | EP | 1 172 041 A2 | 1/2002 |
| CN | 101312659 | A | 11/2008 | EP | 1 172 041 A3 | 1/2002 |
| CN | 101312660 | A | 11/2008 | EP | 1 172 041 B1 | 1/2002 |
| CN | 101312662 | A | 11/2008 | EP | 1 172 041 B2 | 1/2002 |
| CN | 101312663 | A | 11/2008 | EP | 1 172 041 B9 | 1/2002 |
| CN | 101330833 | A | 12/2008 | EP | 1 173 066 A1 | 1/2002 |
| CN | 101340821 | A | 1/2009 | EP | 1 178 811 A1 | 2/2002 |
| CN | 101340824 | A | 1/2009 | EP | 0 948 265 B1 | 4/2002 |
| CN | 101340826 | A | 1/2009 | EP | 0 923 382 B1 | 5/2002 |
| CN | 101340827 | A | 1/2009 | EP | 1 228 769 A1 | 8/2002 |
| CN | 101346074 | A | 1/2009 | EP | 1 259 128 A1 | 11/2002 |
| CN | 101365347 | A | 2/2009 | EP | 1 281 323 A1 | 2/2003 |
| CN | 101365348 | A | 2/2009 | EP | 1 281 323 A4 | 2/2003 |
| CN | 101378667 | A | 3/2009 | EP | 1 328 280 A1 | 7/2003 |
| CN | 101394756 | A | 3/2009 | EP | 1 390 071 A2 | 2/2004 |
| CN | 101472485 | A | 7/2009 | EP | 0 743 011 B1 | 3/2004 |
| CN | 101500435 | A | 8/2009 | EP | 1 259 128 A4 | 3/2004 |
| CN | 101553133 | A | 10/2009 | EP | 1 463 515 A2 | 10/2004 |
| CN | 101631476 | A | 1/2010 | EP | 1 463 515 A4 | 1/2005 |
| CN | 101632434 | A | 1/2010 | EP | 1 496 871 A1 | 1/2005 |
| CN | 101632435 | A | 1/2010 | EP | 1 075 188 B1 | 11/2005 |
| CN | 1655769 | B | 5/2010 | EP | 1 590 004 A2 | 11/2005 |
| CN | 101731623 | A | 6/2010 | EP | 1 633 211 A1 | 3/2006 |
| CN | 101889027 | A | 11/2010 | EP | 1 681 937 A1 | 7/2006 |
| CN | 1787750 | B | 12/2010 | EP | 1 328 280 B1 | 8/2006 |
| CN | 101909468 | A | 12/2010 | EP | 1 694 312 A1 | 8/2006 |
| CN | 101919827 | A | 12/2010 | EP | 1 732 401 A2 | 12/2006 |
| CN | 101925307 | A | 12/2010 | EP | 1 178 811 B1 | 2/2007 |
| CN | 101938911 | A | 1/2011 | EP | 1 786 272 A1 | 5/2007 |
| CN | 1852659 | B | 2/2011 | EP | 1 791 433 A2 | 6/2007 |
| CN | 1695488 | B | 3/2011 | EP | 1 806 971 A1 | 7/2007 |
| CN | 102077854 | A | 6/2011 | EP | 1 858 555 A2 | 11/2007 |
| CN | 102077939 | A | 6/2011 | EP | 1 876 914 A2 | 1/2008 |
| CN | 102077940 | A | 6/2011 | EP | 1 877 094 A1 | 1/2008 |
| CN | 102077944 | A | 6/2011 | EP | 1 906 759 A2 | 4/2008 |
| CN | 102131395 | A | 7/2011 | EP | 1 694 312 B1 | 5/2008 |
| CN | 1777415 | B | 11/2011 | EP | 1 924 153 A2 | 5/2008 |
| CN | 101306011 | B | 11/2011 | EP | 1 924 157 A2 | 5/2008 |
| CN | 102264246 | A | 11/2011 | EP | 1 931 222 A2 | 6/2008 |
| CN | 102308994 | A | 1/2012 | EP | 1 959 744 A1 | 8/2008 |
| CN | 102316752 | A | 1/2012 | EP | 1 959 754 A1 | 8/2008 |
| DE | 2472827 | A1 | 9/1975 | EP | 1 959 755 A1 | 8/2008 |
| DE | 2527632 | A1 | 1/1976 | EP | 1 959 756 A1 | 8/2008 |
| DE | 10 2010 038 644 | A1 | 7/2011 | EP | 1 959 757 A2 | 8/2008 |
| DK | 61775 | A | 9/1975 | EP | 1 959 758 A2 | 8/2008 |
| DK | 123486 | A | 9/1986 | EP | 1 959 759 A2 | 8/2008 |
| EE | 9900266 | A | 2/2000 | EP | 1 959 760 A1 | 8/2008 |
| EE | 03659 | B1 | 4/2002 | EP | 1 959 761 A1 | 8/2008 |
| EP | 0 046 639 | A1 | 3/1982 | EP | 1 959 762 A2 | 8/2008 |
| EP | 0 195 730 | A2 | 9/1986 | EP | 1 959 763 A1 | 8/2008 |

| | | | | | | |
|---|---|---|---|---|---|---|
| EP | 1 496 871 | B1 | 9/2008 | JP | 11196761 | A | 7/1990 |
| EP | 1 962 616 | A2 | 9/2008 | JP | 3-183457 | | 8/1991 |
| EP | 1 965 668 | A2 | 9/2008 | JP | 4228030 | A | 8/1992 |
| EP | 1 968 399 | A1 | 9/2008 | JP | 6237783 | A | 8/1994 |
| EP | 1 968 400 | A1 | 9/2008 | JP | 7067577 | A | 3/1995 |
| EP | 1 971 221 | A1 | 9/2008 | JP | 7-90002 | A | 4/1995 |
| EP | 1 971 223 | A2 | 9/2008 | JP | 9103264 | A | 4/1997 |
| EP | 1 971 224 | A1 | 9/2008 | JP | 9103265 | A | 4/1997 |
| EP | 1 971 225 | A1 | 9/2008 | JP | H 09506342 | | 6/1997 |
| EP | 1 971 226 | A2 | 9/2008 | JP | 10042803 | A | 2/1998 |
| EP | 1 971 227 | A2 | 9/2008 | JP | 2882895 | B2 | 4/1999 |
| EP | 1 971 232 | A1 | 9/2008 | JP | 2939491 | B2 | 8/1999 |
| EP | 1 971 315 | A2 | 9/2008 | JP | 3043070 | B2 | 5/2000 |
| EP | 1 973 419 | A2 | 10/2008 | JP | 2001-509013 | | 7/2001 |
| EP | 1 981 349 | A2 | 10/2008 | JP | 2002037744 | A * | 2/2002 |
| EP | 1 981 484 | A2 | 10/2008 | JP | 2002-511051 | | 4/2002 |
| EP | 1 990 045 | A1 | 11/2008 | JP | 2002-512929 | | 5/2002 |
| EP | 1 993 386 | A2 | 11/2008 | JP | 2003-500361 | | 1/2003 |
| EP | 2 007 224 | A2 | 12/2008 | JP | 2003-534777 | | 11/2003 |
| EP | 1 590 004 | B1 | 1/2009 | JP | 2004-512306 | | 4/2004 |
| EP | 2 065 046 | A1 | 6/2009 | JP | 2005-29513 | | 2/2005 |
| EP | 2 070 551 | A1 | 6/2009 | JP | 2005-503332 | | 2/2005 |
| EP | 2 091 355 | A2 | 8/2009 | JP | 2005-526819 | | 9/2005 |
| EP | 2 124 608 | A2 | 12/2009 | JP | 2005-348731 | | 12/2005 |
| EP | 1 993 386 | A4 | 5/2010 | JP | 2006-516995 | | 7/2006 |
| EP | 1 633 211 | B1 | 6/2010 | JP | 2006-524193 | | 10/2006 |
| EP | 2 230 940 | A1 | 9/2010 | JP | 2006-342085 | | 12/2006 |
| EP | 2 230 941 | A1 | 9/2010 | JP | 2006-527700 | | 12/2006 |
| EP | 2 249 666 | A1 | 11/2010 | JP | 2007-508822 | | 4/2007 |
| EP | 2 328 418 | A1 | 6/2011 | JP | 2007-131620 | | 5/2007 |
| EP | 2 337 458 | A1 | 6/2011 | JP | 2007-520232 | | 7/2007 |
| EP | 1 281 323 | B1 | 7/2011 | JP | 2007-246541 | | 9/2007 |
| EP | 2 346 356 | A1 | 7/2011 | JP | 4059908 | B2 | 12/2007 |
| EP | 2 389 075 | A1 | 11/2011 | JP | 2008-509665 | | 4/2008 |
| EP | 1 681 937 | A4 | 1/2012 | JP | 2008-509922 | | 4/2008 |
| EP | 2 413 713 | A1 | 2/2012 | JP | 2008-183013 | | 8/2008 |
| ES | 8702882 | A1 | 4/1987 | JP | 2008-532555 | | 8/2008 |
| ES | 8707491 | A1 | 10/1987 | JP | 2008-537678 | | 9/2008 |
| ES | 2369102 | A1 | 11/2011 | JP | 2008-539729 | | 11/2008 |
| FI | 910534 | A | 8/1991 | JP | 2009-500034 | | 1/2009 |
| FI | 911683 | A | 10/1991 | JP | 2009-504188 | | 2/2009 |
| FI | 943296 | A | 1/1995 | JP | 2009-504765 | | 2/2009 |
| FI | 962203 | A | 7/1996 | JP | 2009-517020 | | 4/2009 |
| FI | 965251 | A | 7/1998 | JP | 2009-517021 | | 4/2009 |
| FI | 20090217 | A | 5/2009 | JP | 2009-517023 | | 4/2009 |
| FI | 120290 | B1 | 9/2009 | JP | 2009-517024 | | 4/2009 |
| FR | 2 263 704 | A1 | 10/1975 | JP | 2009-517025 | | 4/2009 |
| FR | 2 275 153 | A1 | 1/1976 | JP | 2009-517026 | | 4/2009 |
| FR | 2 275 153 | B1 | 10/1978 | JP | 2009-517027 | | 4/2009 |
| FR | 2 263 704 | B1 | 12/1978 | JP | 2009-517028 | | 4/2009 |
| FR | 2 579 201 | A1 | 9/1986 | JP | 2009-517029 | | 4/2009 |
| FR | 2 579 202 | A1 | 9/1986 | JP | 2009-517030 | | 4/2009 |
| FR | 2 579 201 | B1 | 5/1987 | JP | 2009-517031 | | 4/2009 |
| FR | 2 597 096 | A1 | 10/1987 | JP | 2009-517032 | | 4/2009 |
| FR | 2 579 202 | B1 | 4/1988 | JP | 2009-517033 | | 4/2009 |
| FR | 2 606 404 | A2 | 5/1988 | JP | 2009-517034 | | 4/2009 |
| FR | 2 597 096 | B1 | 6/1988 | JP | 2009-517035 | | 4/2009 |
| FR | 2 606 404 | B2 | 11/1991 | JP | 2009-517036 | | 4/2009 |
| FR | 2 690 445 | A1 | 10/1993 | JP | 2009-517038 | | 4/2009 |
| FR | 2 690 445 | B1 | 11/1994 | JP | 2009-517039 | | 4/2009 |
| GB | 1 471 398 | A | 4/1977 | JP | 2009-517040 | | 4/2009 |
| GB | 1 480 967 | A | 7/1977 | JP | 2009-517041 | | 4/2009 |
| GB | 2 416 981 | A | 2/2006 | JP | 2009-517042 | | 4/2009 |
| GB | 2 418 856 | A | 4/2006 | JP | 2009-517043 | | 4/2009 |
| GB | 2 418 856 | A8 | 4/2006 | JP | 2009-517044 | | 4/2009 |
| GB | 2 418 856 | B | 8/2007 | JP | 2009-517384 | | 4/2009 |
| GB | 2 418 856 | B8 | 8/2007 | JP | 2009-517385 | | 4/2009 |
| GB | 2474937 | A | 5/2011 | JP | 2009-523407 | | 6/2009 |
| GB | 2474938 | A | 5/2011 | JP | 2009-149621 | | 7/2009 |
| GB | 2474939 | A | 5/2011 | JP | 2009-524575 | | 7/2009 |
| GB | 2474940 | A | 5/2011 | JP | 2009-527252 | | 7/2009 |
| GB | 2474941 | A | 5/2011 | JP | 4302318 | B2 | 7/2009 |
| GR | 860583 | A1 | 7/1986 | JP | 2009-533490 | | 9/2009 |
| IE | 910368 | A1 | 8/1991 | JP | 2010-508823 | | 3/2010 |
| JP | 51017315 | A | 2/1976 | JP | 2010-516246 | | 5/2010 |
| JP | 57-46920 | | 3/1982 | JP | 2010-285447 | | 12/2010 |
| JP | 61219352 | A | 9/1986 | JP | 4607261 | B2 | 1/2011 |
| JP | 61219353 | A | 9/1986 | JP | 4615812 | B2 | 1/2011 |
| JP | 63112964 | A | 5/1988 | JP | 2011-67220 | | 4/2011 |

| | | | | | | |
|---|---|---|---|---|---|---|
| JP | 2011-87597 | 5/2011 | | WO | WO 2006/107820 A2 | 10/2006 |
| JP | 2011-98982 | 5/2011 | | WO | WO 2006/107820 A3 | 10/2006 |
| JP | 2011-115177 | 6/2011 | | WO | WO 2006/119286 A1 | 11/2006 |
| JP | 2011-135889 | 7/2011 | | WO | WO 2007/008384 A2 | 1/2007 |
| JP | 4717311 B2 | 7/2011 | | WO | WO 2007/008384 A3 | 1/2007 |
| JP | 4741625 B2 | 8/2011 | | WO | WO 2007/022312 A2 | 2/2007 |
| JP | 4790220 B2 | 10/2011 | | WO | WO 2007/022312 A3 | 2/2007 |
| JP | 2011-254834 | 12/2011 | | WO | WO 2007/022313 A2 | 2/2007 |
| JP | 2012-16356 | 1/2012 | | WO | WO 2007/022313 A3 | 2/2007 |
| KR | 930004456 B1 | 5/1993 | | WO | WO 2007/022341 A2 | 2/2007 |
| KR | 0157425 B1 | 10/1998 | | WO | WO 2007/022341 A3 | 2/2007 |
| KR | 2000-0029878 | 5/2000 | | WO | WO 2007/039294 A2 | 4/2007 |
| KR | 2000-0069761 | 11/2000 | | WO | WO 2007/039294 A3 | 4/2007 |
| KR | 2002-0011991 | 2/2002 | | WO | WO 2007/043656 A1 | 4/2007 |
| KR | 2002-0086556 | 11/2002 | | WO | WO 2007/044547 A1 | 4/2007 |
| KR | 10-2003-0003272 | 1/2003 | | WO | WO 2007/044580 A1 | 4/2007 |
| KR | 10-2004-0040890 | 5/2004 | | WO | WO 2007/044611 A2 | 4/2007 |
| KR | 10-0450097 B1 | 9/2004 | | WO | WO 2007/044611 A3 | 4/2007 |
| KR | 10-2005-0025151 A | 3/2005 | | WO | WO 2007/044637 A1 | 4/2007 |
| KR | 10-0541324 B1 | 1/2006 | | WO | WO 2007/044638 A1 | 4/2007 |
| KR | 10-0689118 B1 | 3/2007 | | WO | WO 2007/044663 A1 | 4/2007 |
| KR | 10-0729478 B1 | 6/2007 | | WO | WO 2007/044665 A2 | 4/2007 |
| KR | 10-2008-0003796 | 1/2008 | | WO | WO 2007/044665 A3 | 4/2007 |
| KR | 10-2008-0007449 | 1/2008 | | WO | WO 2007/044723 A2 | 4/2007 |
| KR | 10-2008-055788 | 6/2008 | | WO | WO 2007/044723 A3 | 4/2007 |
| KR | 10-2008-0067384 A | 7/2008 | | WO | WO 2007/044737 A2 | 4/2007 |
| KR | 10-2008-0098616 | 11/2008 | | WO | WO 2007/044737 A3 | 4/2007 |
| KR | 10-2009-0029699 A | 3/2009 | | WO | WO 2007/061753 A2 | 5/2007 |
| KR | 10-2010-0123780 A | 11/2010 | | WO | WO 2007/061753 A3 | 5/2007 |
| NL | 7501972 A | 9/1975 | | WO | WO 2007/061757 A1 | 5/2007 |
| NL | 7507403 A | 12/1975 | | WO | WO 2007/061794 A2 | 5/2007 |
| PT | 82216 A | 4/1986 | | WO | WO 2007/061794 A3 | 5/2007 |
| PT | 82216 B | 8/1987 | | WO | WO 2007/061796 A2 | 5/2007 |
| PT | 96660 A | 10/1991 | | WO | WO 2007/061796 A3 | 5/2007 |
| PT | 948265 E | 8/2003 | | WO | WO 2007/061797 A2 | 5/2007 |
| RU | 2009109859 A | 9/2010 | | WO | WO 2007/061797 A3 | 5/2007 |
| RU | 2 403 809 C1 | 11/2010 | | WO | WO 2007/061802 A1 | 5/2007 |
| SE | 7501886 A | 9/1975 | | WO | WO 2007/061803 A1 | 5/2007 |
| SE | 404289 B | 10/1978 | | WO | WO 2007/061804 A2 | 5/2007 |
| SE | 404289 C | 1/1979 | | WO | WO 2007/061804 A3 | 5/2007 |
| WO | WO 91/08679 A1 | 6/1991 | | WO | WO 2007/061809 A2 | 5/2007 |
| WO | WO 95/14531 A1 | 6/1995 | | WO | WO 2007/061809 A3 | 5/2007 |
| WO | WO 95/20323 A1 | 8/1995 | | WO | WO 2007/061810 A2 | 5/2007 |
| WO | WO 96/29889 A1 | 10/1996 | | WO | WO 2007/061810 A3 | 5/2007 |
| WO | WO 98/06418 A1 | 2/1998 | | WO | WO 2007/061858 A1 | 5/2007 |
| WO | WO 98/28989 A1 | 7/1998 | | WO | WO 2007/061859 A1 | 5/2007 |
| WO | WO 98/28990 A1 | 7/1998 | | WO | WO 2007/061860 A1 | 5/2007 |
| WO | WO 99/56556 A1 | 11/1999 | | WO | WO 2007/061860 A8 | 5/2007 |
| WO | WO 00/64268 A1 | 11/2000 | | WO | WO 2007/061861 A2 | 5/2007 |
| WO | WO 00/71137 A1 | 11/2000 | | WO | WO 2007/061861 A3 | 5/2007 |
| WO | WO 01/62108 A1 | 8/2001 | | WO | WO 2007/061871 A1 | 5/2007 |
| WO | WO 01/84948 A1 | 11/2001 | | WO | WO 2007/061872 A2 | 5/2007 |
| WO | WO 01/87341 A1 | 11/2001 | | WO | WO 2007/061872 A3 | 5/2007 |
| WO | WO 02/34271 A1 | 5/2002 | | WO | WO 2007/061873 A1 | 5/2007 |
| WO | WO 02/078463 A1 | 10/2002 | | WO | WO 2007/061898 A1 | 5/2007 |
| WO | WO 03/049689 A2 | 6/2003 | | WO | WO 2007/061900 A1 | 5/2007 |
| WO | WO 03/049689 A3 | 6/2003 | | WO | WO 2007/061907 A2 | 5/2007 |
| WO | WO 03/084516 A1 | 10/2003 | | WO | WO 2007/061907 A3 | 5/2007 |
| WO | WO 2004/057985 A2 | 7/2004 | | WO | WO 2007/061908 A1 | 5/2007 |
| WO | WO 2004/057985 A3 | 7/2004 | | WO | WO 2007/061911 A2 | 5/2007 |
| WO | WO 2004/069179 A2 | 8/2004 | | WO | WO 2007/061911 A3 | 5/2007 |
| WO | WO 2004/069179 A3 | 8/2004 | | WO | WO 2007/061912 A2 | 5/2007 |
| WO | WO 2004/093862 A1 | 11/2004 | | WO | WO 2007/061912 A3 | 5/2007 |
| WO | WO 2004/093863 A1 | 11/2004 | | WO | WO 2007/070224 A2 | 6/2007 |
| WO | WO 2004/110178 A1 | 12/2004 | | WO | WO 2007/070224 A3 | 6/2007 |
| WO | WO 2004/112773 A1 | 12/2004 | | WO | WO 2007/098092 A2 | 8/2007 |
| WO | WO 2005/002536 A1 | 1/2005 | | WO | WO 2007/098092 A3 | 8/2007 |
| WO | WO 2005/036971 A1 | 4/2005 | | WO | WO 2007/117281 A2 | 10/2007 |
| WO | WO 2005/048995 A1 | 6/2005 | | WO | WO 2007/117281 A3 | 10/2007 |
| WO | WO 2005/076821 A2 | 8/2005 | | WO | WO 2007/120500 A2 | 10/2007 |
| WO | WO 2005/076821 A3 | 8/2005 | | WO | WO 2007/120500 A3 | 10/2007 |
| WO | WO 2006/016170 A2 | 2/2006 | | WO | WO 2007/142680 A1 | 12/2007 |
| WO | WO 2006/016170 A3 | 2/2006 | | WO | WO 2008/056967 A1 | 5/2008 |
| WO | WO 2006/020686 A1 | 2/2006 | | WO | WO 2008/057965 A2 | 5/2008 |
| WO | WO 2006/020754 A1 | 2/2006 | | WO | WO 2008/057965 A3 | 5/2008 |
| WO | WO 02/067986 A2 | 9/2006 | | WO | WO 2008/087607 A2 | 7/2008 |
| WO | WO 02/067986 A3 | 9/2006 | | WO | WO 2008/087607 A3 | 7/2008 |
| WO | WO 2006/102108 A2 | 9/2006 | | WO | WO 2009/072884 A1 | 6/2009 |
| WO | WO 2006/102108 A3 | 9/2006 | | WO | WO 2009/072885 A1 | 6/2009 |

| | | | |
|---|---|---|---|
| WO | WO 2009/072886 A1 | 6/2009 |
| WO | WO 2009/079537 A1 | 6/2009 |
| WO | WO 2009/086685 A1 | 7/2009 |
| WO | WO 2010/022764 A1 | 3/2010 |
| WO | WO 2010/043332 A1 | 4/2010 |
| WO | WO 2010/047581 A1 | 4/2010 |
| WO | WO 2010/047597 A1 | 4/2010 |
| WO | WO 2010/080557 A1 | 7/2010 |
| WO | WO 2010/114627 A1 | 10/2010 |
| WO | WO 2011/024199 A1 | 3/2011 |
| WO | WO 2011/024199 A4 | 3/2011 |
| WO | WO 2011/031617 A2 | 3/2011 |
| WO | WO 2011/031617 A3 | 3/2011 |
| WO | WO 2011/031621 A2 | 3/2011 |
| WO | WO 2011/031621 A3 | 3/2011 |
| WO | WO 2011/051650 A1 | 5/2011 |
| WO | WO 2011/051651 A1 | 5/2011 |
| WO | WO 2011/051652 A1 | 5/2011 |
| WO | WO 2011/051653 A1 | 5/2011 |
| WO | WO 2011/051654 A1 | 5/2011 |
| WO | WO 2011/113984 A1 | 9/2011 |

OTHER PUBLICATIONS

James M. Falko, et al., "Gastric Inhibitory Polypeptide (GIP) Stimulated by Fat Ingestion in Man", J. Clin. Endocrinol. Metab. vol. 41, No. 2, 1975, pp. 260-265.

Oda Toshitsugu, et al., Digestive Tract—Functions and Pathological Conditions ("Shoukakan Kinou to Byoutai"), 1981, Chugai-Igakusha, pp. 205-216. (with partial English translation).

S. J. Gatenby, et al., "Effect of Partially Depolymerized Guar Gum on Acute Metabolic Variables in Patients with Non-insulin-dependent Diabetes", Diabetic Medicine, vol. 13, 1996, pp. 358-364.

P. R. Ellis[1], et al., "The effect of high-molecular-weight guar gum on net apparent glucose absorption and net apparent insulin and gastric inhibitory polypeptide production in the growing pig: relationship to rheological changes in jejunal digesta", British Journal of Nutrition, vol. 74, 1995, pp. 539-556.

C Simões Nunes[1], et al., "Glucose absorption, hormonal release and hepatic metabolism after guar gum ingestion", Reprod Nutr Dev, vol. 32, 1992, pp. 11-20.

L. M. Morgan, et al., "The effect of soluble- and insoluble-fibre supplementation on post-prandial glucose tolerance, insulin and gastric inhibitory polypeptide secretion in healthy subjects", British Journal of Nutrition, vol. 64, 1990, pp. 103-110.

F. Reuejo[a], et al., "Effects of α-Glucosidase Inhibition and Viscous Fibre on Diabetic Control and Postprandial Gut Hormone Responses", Diabetic Medicine, vol. 7, 1990, pp. 515-520.

L. M. Morgan, et al., "The effect of guar gum on carbohydrate-, fat- and protein-stimulated gut hormone secretion: modification of postprandial gastric inhibitory polypeptide and gastrin responses", British Journal of Nutrition, vol. 53, 1985, pp. 467-475.

Keisuke Tsuji, et al., "Effects of Na-Binding Capacity of Dietary Fibers on Blood Pressure in Spontaneously Hypertensive Rats", Journal of Home Economics of Japan, vol. 39, No. 3, 1988, pp. 187-195.

\* cited by examiner

GIP SECRETION INHIBITOR

FIELD OF THE INVENTION

The present invention relates to a GIP secretion inhibitor which is useful as a medicine or a food product.

BACKGROUND OF THE INVENTION

Gastric inhibitory polypeptide (GIP) is a gastrointestinal hormone having gastric acid secretion inhibitory action or gastric motility inhibitory action, and it is known that secretion thereof is enhanced by lipids and the like in the diet during food intake (Non-Patent Documents 1 to 3). Therefore, a substance inhibiting the secretion of GIP is believed to be useful in the facilitation of digestion or in the improvement of a heavy feeling in the stomach. Previous studies have reported that 3-bromo-5-methyl-2-phenylpyrazolo[1,5-a]pyrimidin-7-ol (BMPP) inhibited functions of GIP, and that guar gum and the like inhibited postprandial secretion of GIP (Patent Document 1 and Non-Patent Documents 4 to 9).

However, the former substance BMPP has not been verified to have an inhibitory effect on functions of GIP in vivo, while the latter substances guar gum and the like have a problem that their GIP secretion inhibitory effect during lipid ingestion has not been examined. Further, the effect of the above substances on improving a heavy feeling in the stomach or the like is not necessarily satisfactory.

Under such circumstances, the Applicant of the present invention found that when the sodium salt of alginic acid, which is one of the high molecular weight acidic polysaccharides present in brown algae, was fed to a mouse, a postprandial GIP secretion was inhibited, and that the sodium salt of alginic acid can thus serve as a postprandial GIP secretion inhibitor. The Applicant filed a patent application based on the finding (Patent Document 2).

On the other hand, potassium alginate is widely used as a thickening agent for food products or as a gelling agent in the preparations for dental impression, and is also reported to have a hypotensive action which is based on the mechanism of sodium excretion in the body (Non-Patent Document 10).

However, it has not been known that potassium alginate has a very excellent GIP secretion inhibitory action.

[Patent Document 1] WO 01/87341
[Patent Document 2] JP2006-342085
[Non-Patent Document 1] J. C. Brown, et al., Canadian J. Physiol. Pharmacol., 47: 113-114, 1969
[Non-Patent Document 2] J. M. Falko, et al., J. Clin. Endocrinol. Metab. 41(2); 260-265, 1975
[Non-Patent Document 3] Oda Toshitsugu, et al., Digestive Tract—Functions and Pathological conditions ("Shoukakan Kinou to Byoutai"), 1981, Chugai-Igakusha, p. 205-216
[Non-Patent Document4] Gagenby, S J, et al., Diabet. Med., 1996 April; 13(4); 358-64
[Non-Patent Document 5] Ellis P R, et al., Br. J. Nutr. 1995 October; 74(4): 539-56
[Non-Patent Document 6] Simoes Nunes C, et al., Reprod, Nutr. Dev., 1992; 32(1): 11-20
[Non-Patent Document 7] Morgan L M, et al., Br. J. Nutr., 1990 July; 64(1): 103-10
[Non-Patent Document 8] Requejo F, et al., Diabet Med., 1990 July; 7(6):515-20
[Non-Patent Document 9] Morgan, et al., Br. J. Nutr., 1985 May; 53(3): 467-75
[Non-Patent Document 10] Tsuji Keiske, et al., Journal of Home Economics of Japan, Vol. 39, No. 3, Page. 187-195 (1988)

SUMMARY OF THE INVENTION

The present invention provides a postprandial GIP secretion inhibitor, comprising potassium alginate as an active ingredient.

The present invention also provides a method for inhibiting postprandial GIP secretion, which comprises administering potassium alginate to a subject in need thereof or causing a subject in need thereof to consume potassium alginate.

DETAILED DESCRIPTION OF THE INVENTION

In an aspect of the present invention, a GIP secretion inhibitor which is useful as a medicine or a food product is provided.

The inventors of the present invention made a detailed study of the GIP secretion inhibitory action of alginic acid or a salt thereof, and found that the potassium salt of alginic acid notably inhibits postprandial GIP secretion and thus is more useful for the facilitation of digestion or the improvement in a heavy feeling in the stomach, as compared with sodium alginate.

The GAP secretion inhibitor of the present invention can reduce the postprandial secretion of GIP and facilitate digestion and absorption of food, and thereby improving a heavy feeling in the stomach.

Alginic acid is a high molecular weight acidic polysaccharide (molecular weight: several ten thousands to several hundred thousands) containing, as a main constituent sugar, uronic acid (D-mannuronic acid and L-gluronic acid) which is distributed in all of the brown algae as a substance located between cell walls, and has one carboxyl group in one constituent unit. Potassium alginate is a salt formed by binding the carboxyl group of alginic acid and a potassium ion.

The potassium alginate that may be used in the present invention is a low molecular weight potassium alginate having a weight average molecular weight measured by high performance liquid chromatography (HPLC) of 60, 000 or less, preferably 10,000 to 60,000, more preferably 20,000 to 60,000, and even more preferably 20,000 to 50,000. Specifically, in the case where the postprandial GIP secretion inhibitor of the present invention is in the form of an oral liquid preparation, the viscosity of the potassium alginate is preferably low from the viewpoints of producibility, and of the feeling of running down the throat, slipperiness, ease of swallowing or the like at the time of drinking the preparation. In the above embodiment, it is preferable to use a less viscous potassium alginate having a weight average molecular weight of about 10,000 to 50,000, it is more preferable to use a potassium alginate having a weight average molecular weight of 10,000 to 40,000, and it is even more preferable to use a potassium alginate having a weight average molecular weight of 10,000 to 30,000.

The potassium alginate of the present invention can be produced by any methods such as thermal degradation under pressure (JP6-7093), enzymatic degradation (JP2-303468, JP3-94675, JP4-169189, JP6-245767, and JP6-217774) or the like. That is, the potassium alginate of the present invention can be obtained by, for example, converting a high molecular weight potassium alginate or a high molecular weight alginic acid, which serves as the raw material, to a low molecular weight product having a desired molecular weight by thermal degradation under pressure, thermal degradation under normal pressure, enzymatic degradation or the like, and optionally neutralizing, dehydrating and freeze-drying the resultant. The adjustment of the molecular weight can be carried out, for example, in the case of thermal degradation, by controlling the reaction pH, reaction temperature, reaction time, or the like.

The potassium alginate of the present invention thus obtainable has a GIP secretion inhibitory effect. As will be described in the Examples below, the blood GIP level in mice fed with the potassium alginate of the invention was low even after simultaneous consumption of sugars, lipids and proteins. The effect of the potassium alginate of the invention was much more excellent compared to that of sodium alginate. The amount of GIP secretion in mice consumed the potassium alginate of the invention was about a half compared to mice consumed the sodium alginate.

Therefore, the potassium alginate of the present invention can exert effects of reducing the postprandial GIP level, facilitating digestion and absorption, and the like, and is capable of serving as a more useful postprandial GIP secretion inhibitor. The potassium alginate of the present invention can also be used for the manufacture of a postprandial GIP secretion inhibitor.

In regard to the postprandial GIP secretion inhibitor of the present invention, potassium alginate alone can be administered to human or animals in a form of a food product, a medicine or the like. Potassium alginate can also be blended into various food products, medicines, pet feedstuffs and the like and be consumed by human or animals. In the case of using the postprandial GIP secretion inhibitor as a food product, the food product includes foods labeled to inform that they are used for inhibition of gastric acid secretion, facilitation of digestion, improvement in a heavy feeling in the stomach and the like, such as food for cosmetic purpose, food for sick people, and food for specific health maintenance purpose, when used as a medicine, the postprandial GIP secretion inhibitor of the invention may be provided in a form of oral solid preparations such as tablets and granules, or oral liquid preparations such as solutions for internal use and syrups.

Furthermore, in the case of preparing an oral solid preparation, an excipient, and if necessary, a binding agent, a disintegrant, a lubricant, a colorant, a savoring agent, a flavoring agent, and the like may be combined with the potassium alginate of the present invention, and then tables, coated tablets, granules, powders, capsules and the like can be produced by commonly used methods. In the case of preparing an oral liquid preparation, a savoring agent, a buffering agent, a stabilizing agent, a flavoring agent and the like may be combined with the potassium alginate of the present invention, and then solutions for internal use, syrups, elixirs and the like can be produced by commonly used methods.

The amount of the potassium alginate to be incorporated into the various preparations may be usually 0.01 to 100% by weight, preferably 0.1 to 80% by weight, and more preferably, 1 to 50% by weight in the case of preparing a solid preparation, and 0.1 to 20% by weight in the case of preparing a liquid preparation.

The dosage amount (effective amount of consumption) of the postprandial GIP secretion inhibitor or the food product of the present invention (as the amount of potassium alginate) is preferably 0.001 g/kg of body weight or more per day, preferably 0.01 to 1.0 g/kg of body weight per day.

EXAMPLES

Production Example 1

Preparation of Potassium Alginate Having Weight Average Molecular Weight of About 18,000

Potassium alginate (KIMICA ALGIN K-ULV Lot. 6K17001: Kimica Corp.) was prepared into a 2% solution, and the solution was adjusted to pH 4 by adding hydrochloric acid, and thermally degraded under pressure at 120° C. for 25 minutes, Subsequently, potassium hydroxide was added thereto to neutralize the solution to pH 7. Then, ethanol was added to the solution to obtain an 80% ethanol solution, and thus potassium alginate was precipitated. Subsequently, the precipitate was collected by centrifugation (3000 rpm, 10 min), and then dried to obtain the final product. The weight average molecular weight of the final product was measured by the method described hereinbelow, which was 17,951.

Production Example 2

Preparation of Potassium Alginate Having Weight Average Molecular Weight of About 50,000

Alginic acid (DUCKACID A Lot. X-2702: Kibun Food Chemifa Co., Ltd.) was prepared into a 5% solution, and the solution was thermally degraded at 100° C. for 45 minutes. Subsequently, potassium hydroxide was added thereto to neutralize the solution to pH 7. Then, ethanol was added to the solution to obtain an 80% ethanol solution, and thus potassium alginate was precipitated. Subsequently, the precipitate was collected by centrifugation (3000 rpm, 10 min), and then dried to obtain the final product. The weight average molecular weight of the final product was measured by the method described hereinbelow, which was 52,163.

Production Example 3

Preparation of Potassium Alginate Having Weight Average Molecular Weight of About 25,000

Alginic acid (DUCKACID A Lot. X-2702; Kibun Food Chemifa Co., Ltd.) was prepared into a 5% solution, and the solution was thermally degraded at 100° C. for 120 minutes. Subsequently, potassium hydroxide was added thereto to neutralize the solution to pH 7. Then, ethanol was added to the solution to obtain an 80% ethanol solution, and thus potassium alginate was precipitated. Subsequently, the precipitate was collected by centrifugation (3000 rpm, 10 min.), and then dried to obtain the final product. The weight average molecular weight of the final product was measured by the method that will be described later, which was 25,801.

Production Example 4

Preparation of Potassium Alginate Having Weight Average Molecular Weight of About 12,000

Alginic acid (DUCKACID A Lot. X-2702; Kibun Food Chemifa Co., Ltd.) was prepared into a 5% solution, and the solution was thermally degraded at 100° C. for 120 minutes. Subsequently, potassium hydroxide was added thereto to adjust the solution to pH 4, and the resultant was thermally degraded at 100° C. for 540 minutes. Subsequently, potassium hydroxide was added thereto to neutralize the solution to pH 7. Then, ethanol was added to the solution to obtain an 80% ethanol solution, and thus potassium alginate was precipitated. Subsequently, the precipitate was collected by centrifugation (3000 rpm, 10 min), and then dried to obtain the final product. The weight average molecular weight of the final product was measured by the method described hereinbelow, which was 12,471.

Measurement of average molecular weight of alginic acid salt (Method for measuring weight average molecular weight)

The weight average molecular weight of alginic acid salt is measured with high performance liquid chromatography (HPLC). A sample for HPLC analysis is prepared by dissolving 0.1 g alginic acid salt in distilled water to obtain 0.1% solution of constant volume.

The HPLC operation conditions are as follows. To obtain a calibration curve for the calculation of molecular weight, standard pullulan (SHODEX STANDARD P-82 manufactured by Showa Denko Co., Ltd.) is used. A 100 μL analyte for HPLC is injected into the HPLC column, and the weight average molecular weight of alginic acid salt in the sample is calculated from the obtained chromatogram chart.

<Conditions for HPLC operation>

Column: (1) Super AW-L (guide column): manufactured by Tosoh Corp.
(2) TSK-GEL Super AW4000 (GPC column): exclusion limit molecular weight $4\times10^5$ PEO/DMF, length 15 cm, internal diameter 6 mm, manufactured by Tosoh Corp.
(3) TSK-GEL Super AW2500 (GPC column): exclusion limit molecular weight $2\times10^3$ PEO/DMF, length 15 cm, internal diameter 6 mm, manufactured by Tosoh Corp.

These columns are connected in the order of AW-L, AW4000 and AW2500.

Column temperature: 40° C.
Detector: differential refractometer
Mobile phase: 0.2 mol/L of aqueous solution of sodium nitrate
Flow rate: 0.6 mL/min
Amount of injection: 100 μL Test Example 1

GIP Increase Inhibitory Effect of Potassium Alginate (1)

1-1. Test Sample

As for potassium alginate (K alginate), a sample having a weight average molecular weight of 59,474 (Lot. 6K17001, purchased from Kimica Corporation) and a sample having an average molecular weight of 17,951 were used. As a control for comparison, a sample of sodium alginate (Na alginate) having an average molecular weight of 58,000 (Lot. 5N162, purchased from Kimica Corporation) was used.

1-2. Test Animal 10-week old male mice, C57BL/6J Jcl (Japan Crea Co., Ltd.), were used. The number of mice in each group was N=4.

1-3. Preparation and Dosage Amount of Sample Compositions for Oral Administration Glucose (manufactured by Kanto Chemical Co., Inc.) and triolein (glyceryl trioleate: manufactured by Sigma-Aldrich Company) were emulsified using egg lecithin (manufactured by Wako Pure Chemical Industries, Ltd.) and bovine serum albumin (Sigma-Aldrich Company) to prepare an emulsion. The above-described test samples were added to the emulsion to prepare test sample compositions. The final concentrations of each component in the test sample compositions were; 5 (w/w) % of the test sample; 5 (w/w) % of glucose; 5 (w/w) % of triolein; and emulsifiers (0.2 (w/w) % of lecithin and 1.0 (w/w) % of albumin). Control sample composition was prepared in the same manner as tor the test sample compositions, expect that no test sample was added thereto. The amounts of each component administered to the animals were as indicated in the table below.

TABLE 1

Amounts of oral administration to mice

|  | Glucose (mg/g of body weight) | Triolein (mg/g of body weight) | Test sample (mg/g of body weight) |
|---|---|---|---|
| Control sample administered group | 2 | 2 | — |
| Test sample administered group | 2 | 2 | 2 |

1-4. Test on Oral Administration

Mice were tasted overnight and were anesthetized with diethyl ether, and initial blood collection was carried out from the orbital vein using a heparinized hematocrit capillary tube (manufactured by vitrex Medical AS). Subsequently, the control or test sample composition was orally administered through a gastric feeding tube, and after 10 minutes, 30 minutes, 1 hour and 2 hours, blood was collected from the orbital vein under diethyl ether anesthesia.

The blood collected with a heparinized hematocrit capillary tube was stored under ice until plasma separation, and centrifuged at 11000 rpm for 5 minutes to obtain blood plasma. From the obtained blood plasma, the GIP concentration in the blood was measured using a Rat/Mouse GIP (Total) ELISA kit (manufactured by Linco Research/Millipore Corp., ELISA method).

1-5. Results

In regard to the blood GIP levels up to 2 hours after the oral administration of the sample composition, the difference between the maximum value (10 minutes) and the initial value (Δ value) was calculated. The data are shown in Table 2.

As for the statistical significant differences between groups, if significance (P <0.05) was recognized from an analysis of variance, the multiple comparison test (Bonferroni/Dunn method) was performed between the group administered with K alginate (average molecular weight; 59,474) or the group administered with K alginate (average molecular weight: 17,951) and the group administered with Na alginate (average molecular weight: 58,000). The case where the significance level was less than 5% was indicated with the P value, while the case where the significance level was 5% or higher was indicated as N.S. (Non-Significant).

TABLE 2

Postprandial maximum GIP secretion in mice
(value at 10 minutes minus initial value)
Analysis of variance (P < 0.0001)

|  | ΔGIP value (value at 10 min) Average ± S.E. (pg/ml) | Comparison between group administered with Na alginate and group administered with K alginate |
|---|---|---|
| Control group | 749 ± 62 | — |
| Group administered with Na alginate (average molecular weight: 58,000) | 582 ± 11 | — |

TABLE 2-continued

Postprandial maximum GIP secretion in mice
(value at 10 minutes minus initial value)
Analysis of variance (P < 0.0001)

|  | ΔGIP value (value at 10 min) Average ± S.E. (pg/ml) | Comparison between group administered with Na alginate and group administered with K alginate |
|---|---|---|
| Group administered with K alginate (average molecular weight: 59,474) | 293 ± 29 | P < 0.001 |
| Group administered with K alginate (average molecular weight: 17,951) | 340 ± 48 | P < 0.01 |

The maximum GIP values in group administered with K alginate having average molecular weight of 59,474 and in group administered with K alginate having average molecular weight of 17,951 were lower than that in group administered with Na alginate (average molecular weight: 58,000). The result indicates that K alginate has a far more excellent postprandial GIP secretion inhibitory effect than Na alginate.

Test Example 2

GIP Increase Inhibitory Effect of Potassium Alginate (2)

2-1. Test Sample

Potassium alginates (K alginate each having average molecular weights of 12,471, 25,801 and 52,163 were used as test samples.

2-2. Test Animal 10- to 11-week old male mice, C57BL/6J Jcl (Japan Crea Co., Ltd.), were used. The number of mice in each group was N=6.

2-3. Preparation of and Dosage Amount of Sample Compositions for Oral Administration Triolein (glyceryl trioleate: manufactured by Sigma-Aldrich Company) was emulsified using egg lecithin (manufactured by Wako Pure Chemical Industries, Ltd.) and bovine serum albumin (Sigma-Aldrich Company) to prepare an emulsion. The above-described test samples were added to the emulsion to prepare test sample compositions. The final concentrations of each component in the test sample compositions were; 5 (w/w) % of the test sample; 5 (w/w) % of triolein; and emulsifiers (0.2 (w/w) % of lecithin and 1.0 (w/w) % of albumin). Control sample composition was prepared in the same manner as for the test sample compositions, expect that no test sample was added thereto. The amounts of each component administered to the animals were as indicated in Table 3.

TABLE 3

Amounts of oral administration to mice

|  | Triolein (mg/g of body weight) | Test sample (mg/g of body weight) |
|---|---|---|
| Control sample administered group | 2 | — |
| Test sample administered group | 2 | 2 |

2-4. Test on Oral Administration

Mice were fasted overnight and were anesthetized with diethyl ether, and initial blood collection was carried out from the orbital vein using a heparinized hematocrit capillary tube (manufactured by Vitrex Medical AS). Subsequently, the control or test sample composition was orally administered through a gastric feeding tube, and after 10 minutes, 30 minutes, 1 hour and 2 hours, blood was collected from the orbital vein under diethyl ether anesthesia.

The blood collected with a heparinized hematocrit capillary tube was stored under ice until plasma separation, and centrifuged at 11000 rpm for 5 minutes to obtain blood plasma. From the obtained blood plasma, the GIP concentration in the blood was measured using a Rat/Mouse GIP (Total) ELISA kit (manufactured by Linco Research/Millipore Corp., ELISA method).

2-5. Results

In regard to the blood GIP levels up to 2 hours after the oral administration of the sample composition, the difference between the maximum value (10 minutes) and the initial value (Δ value) was calculated. The data are shown in Table 4.

As for the statistical significant differences between groups, if significance (P <0.05) was recognized from an analysis of variance, the multiple comparison test (Bonferroni/Dunn method) was performed between the respective groups. The case where the significance level was less than 5% was indicated with the P value, while the case where the significance level was 5% or higher was indicated as N.S. (Non-Significant).

TABLE 4

Postprandial maximum GIP secretion in mice
(value at 10 minutes minus initial value)

Analysis of variance (P < 0.01)

|  | ΔGIP value (value at 10 min) Average ± S.E. (pg/ml) | Comparison to control group | Comparison between group administered with K alginate having average molecular weight of 52,163 |
|---|---|---|---|
| Group administered with control | 204 ± 40 | — | P < 0.001 |
| Group administered with K alginate (average molecular weight: 12,471) | 79 ± 18 | P < 0.01 | N.S. |
| Group administered with K alginate (average molecular weight: 25,801) | 86 ± 21 | P < 0.01 | N.S. |
| Group administered with K alginate (average molecular weight: 52,163) | 43 ± 17 | P < 0.001 | — |

The maximum GIP values in group administered with K alginate (average molecular weight: 12,471), K alginate (average molecular weight: 25,801) or K alginate (average molecular weight: 52,163) were lower than that Ln the group administered with control sample. Furthermore, there was no difference between the maximum GIP values between the K alginate having average molecular weight of 52,163), K alginate having average molecular weight of 25,801) and K alginate having average molecular weight of 12,471), which indicates that all of them have an excellent postprandial GIP secretion inhibitory effect.

Test Example 3

Viscosity of Potassium Alginate (Molecular Weight about 12,000 to 60,000)

3-1. Test Sample

Potassium alginates (K alginate) each having average molecular weights of 12,471, 25,801 and 59,474 were used as test samples. These K alginates were the same test samples as those used in Test Example 1 and 2.

3-2. Method for Measuring Viscosity

A 20 (w/w) % aqueous solution of each of the test samples was prepared, 70 g of the aqueous solution was placed in a 100-ml beaker, and the viscosity of the solution was measured at a liquid temperature of 25±1° C. A hand-held viscometer, PM-2B (manufactured by Malcom Co., Ltd., range of measurement 0.2 to 19.99 Pa·S) was used.

3-3. Results

The results are shown in Table 5.

TABLE 5

| Test sample (20 (w/w) % aqueous solution) | Average molecular weight | Viscosity (Pa · S) |
|---|---|---|
| Na alginate | 58,000 | 0.41 |
| K alginate | 59,474 | 0.41 |
| K alginate | 25,801 | 0.2 or less |
| K alginate | 12,471 | 0.2 or less |

The K alginate (average molecular weight: 59,474) exhibited the same degree of viscousness as that of the Na alginate (average molecular weight: 58,000). The viscosities of the K alginates each having average molecular weights of 25,801 and 12,471 were lower than that of the K alginate having average molecular weight of 59,474).

In the case of producing a preparation in the form of an oral liquid preparation using a water-soluble edible fiber having certain viscousness, such as K alginate, it is more favorable to prepare a preparation having lower viscosity, from the viewpoint of producibility. Furthermore, even upon drinking the preparation, a preparation having lower viscosity is preferred also from the viewpoints of the feeling of running down the throat, slipperiness, ease of swallowing, and the like. The K alginates (average molecular weights: 25,801 and 12,471) are of low viscosity, and also have good postprandial GIP secretion reducing action. Thus, these K alginates are adequate for using in liquid preparations.

What is claimed is:

1. A method for inhibiting postprandial GIP secretion, which comprises administering potassium alginate to a subject in need thereof or causing a subject in need thereof to consume potassium alginate.

2. The method according to claim 1, wherein the weight average molecular weight of the potassium alginate is 10,000 to 60,000.

3. The method according to claim 1, wherein the weight average molecular weight of the potassium alginate is 10,000 to 50,000.

4. The method according to claim 1, wherein the weight average molecular weight of the potassium alginate is 20,000 to 50,000.

5. The method according to claim 1, wherein the weight average molecular weight of the potassium alginate is 10,000 to 40,000.

6. The method according to claim 1, wherein the weight average molecular weight of the potassium alginate is 10,000 to 30,000.

7. The method according to claim 1, wherein the subject is a human.

8. The method according to claim 1, wherein the subject is an animal.

9. The method according to claim 1, wherein the potassium alginate is contained in a food product.

10. The method according to claim 1, wherein the potassium alginate is contained in a medicine.

11. The method according to claim 10, wherein the medicine is an oral solid preparation.

12. The method according to claim 11, wherein potassium alginate is incorporated into said oral solid preparation at an amount ranging from 1 to 50% by weight.

13. The method according to claim 10, wherein the medicine is an oral liquid preparation.

14. The method according to claim 13, wherein potassium alginate is incorporated into said oral liquid preparation at an amount ranging from 0.1 to 20% by weight.

15. The method according to claim 1, wherein the potassium alginate is contained in a pet feedstuff.

16. The method according to claim 1, wherein the dosage of potassium alginate administered to said subject is at least 0.001 g/kg of body weight per day.

17. The method according to claim 1, wherein the dosage of potassium alginate administered to said subject ranges from 0.01 to 1.0 g/kg of body weight per day.

* * * * *